(12) United States Patent
Sidduri et al.

(10) Patent No.: US 6,420,600 B1
(45) Date of Patent: Jul. 16, 2002

(54) PHENYLALANINOL DERIVATIVES

(75) Inventors: Achytharao Sidduri, Livingston; Jefferson Wright Tilley, North Caldwell, both of NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/506,062

(22) Filed: Feb. 17, 2000

Related U.S. Application Data

(60) Provisional application No. 60/120,498, filed on Feb. 18, 1999.

(51) Int. Cl.$^7$ ............... C07C 229/00; C07C 239/00; C07C 241/00; C07C 243/00; C07C 249/00
(52) U.S. Cl. ............... 562/575; 562/576; 564/149; 564/151; 564/123
(58) Field of Search ............... 564/151, 123, 564/149; 562/575, 576

(56) References Cited

U.S. PATENT DOCUMENTS

| | | | |
|---|---|---|---|
| 3,023,235 A | 2/1962 | Leonard | 260/519 |
| 3,527,793 A | 9/1970 | Holdrege | 260/471 |
| 5,463,116 A | 10/1995 | Sumikawa et al. | 562/450 |
| 5,804,595 A | 9/1998 | Portoghese et al. | 514/428 |

FOREIGN PATENT DOCUMENTS

| | | | |
|---|---|---|---|
| CA | 2004127 | | 6/1990 |
| DK | 195 48 709 | | 7/1997 |
| DK | 196 54 483 | | 1/1998 |
| EP | 0 207 681 | | 1/1987 |
| EP | 848000 | * | 6/1998 |
| WO | WO 95/35296 | | 12/1995 |
| WO | WO 96/22966 | | 8/1996 |
| WO | WO 97/36859 | | 10/1997 |
| WO | 9736859 | * | 10/1997 |
| WO | WO 97/36862 | | 10/1997 |
| WO | 98 53814 | | 12/1998 |
| WO | WO 99/10312 | | 3/1999 |
| WO | WO 9910312 | * | 3/1999 |
| WO | WO 99/10313 | | 3/1999 |
| WO | WO 99/43642 | | 9/1999 |
| WO | WO 99/48879 | | 9/1999 |
| WO | WO 99/61465 | | 12/1999 |

OTHER PUBLICATIONS

Org. Chem.: Morrison & Boyd, pp. 788,838,839, 1998.*
E. Von Arx, et al., J. Chromatography 1976, vol. 120, pp. 224–228.
Patent Abstracts of Japan vol. 013, No. 029 (C–562), Jan. 23, 1989—JP 63233963 A, Showa Denko.
Abstract corresponding to JP63233963.
Patani, et al., Chemical Reviews, vol. 96, pp. 3147–3176 (1996.
Advanced Organic Chemistry, $2^{nd}$ Edition, McGraw Hill, pp. 246–259 (1977).
Scheibey, S., et al. Bull. Soc. Chim. Belg. 1978, vol. 87, pp. 229–238.
Cava, M.P., et al. Tetrahedron 1985, vol. 41, pp. 5061–5087.
Meyers, A. I., et al. J. Org. Chem. 1978, vol. 43 pp. 1372–1379.
English Abstract for Document B2—DE 196 54 483.
English Abstract for Document B1—DE 195 48 709.

* cited by examiner

*Primary Examiner*—Mukund J. Shah
*Assistant Examiner*—Sudhaker B. Patel
(74) *Attorney, Agent, or Firm*—George W. Johnston; Dennis P. Tramaloni

(57) ABSTRACT

It has been discovered that compounds of the formula:

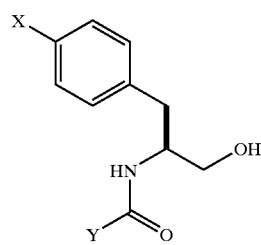

and the pharmaceutically acceptable salts and esters thereof wherein X and Y are as defined below, are more readily absorbed and more bioavailable than the corresponding carboxylic acids from which they are derived, both of which are effective inhibitors of the binding of VCAM-1 to VLA-4 in vivo and are useful in treating inflammation in inflammatory diseases in which such binding acts to bring on the inflammation.

15 Claims, No Drawings

PHENYLALANINOL DERIVATIVES

CROSS REFERENCE TO RELATED APPLICATIONS

This application is related to:

Chen, et al. U.S. Ser. No. 09/138,353 filed Aug. 21, 1998, Title: N-ALKANOYLPHENYLALANINE DERIVATIVES; and Chen, et al. U.S. Ser. No. 09/137,798 filed Aug. 21, 1998, Title: N-AROYLPHENYLALANINE DERIVATIVES.

This application claims benefit to U.S. Provisional application Ser. No. 60/120,498, filed Feb. 28, 1999.

BACKGROUND OF THE INVENTION

Vascular cell adhesion molecule-1 (VCAM-1), a member of the immunoglobulin (Ig) supergene family, is expressed on activated, but not resting, endothelium. The integrin VLA-4 ($a_4 b_1$), which is expressed on many cell types including circulating lymphocytes, eosinophils, basophils, and monocytes, but not neutrophils, is the principal receptor for VCAM-1. Antibodies to VCAM-1 or VLA-4 can block the adhesion of these mononuclear leukocytes, as well as melanoma cells, to activated endothelium in vitro. Antibodies to either protein have been effective at inhibiting leukocyte infiltration and preventing tissue damage in several animal models of inflammation. Anti-VLA-4 monoclonal antibodies have been shown to block T-cell emigration in adjuvant-induced arthritis, prevent eosinophil accumulation and bronchoconstriction in models of asthma, and reduce paralysis and inhibit monocyte and lymphocyte infiltration in experimental autoimmune encephalitis (EAE). Anti-VCAM-1 monoclonal antibodies have been shown to prolong the survival time of cardiac allografts. Recent studies have demonstrated that anti-VLA-4 mAbs can prevent insulitis and diabetes in non-obese diabetic mice, and significantly attenuate inflammation in the cotton-top tamarin model of colitis.

Thus, compounds which inhibit the interaction between $\alpha_4$-containing integrins, such as VLA-4, and VCAM-1 are useful as therapeutic agents for the treatment of inflammation caused by chronic inflammatory diseases such as rheumatoid arthritis (RA), multiple sclerosis (MS), pulmonary inflammation (e.g., asthma), and inflammatory bowel disease (IBD).

These applications disclose the acids and esters corresponding to the alcohol compounds of this invention and the method of preparing these acids and esters. The disclosure of these U.S. patent applications are hereby incorporated by reference.

SUMMARY OF THE INVENTION

It has been discovered that compounds of the formula:

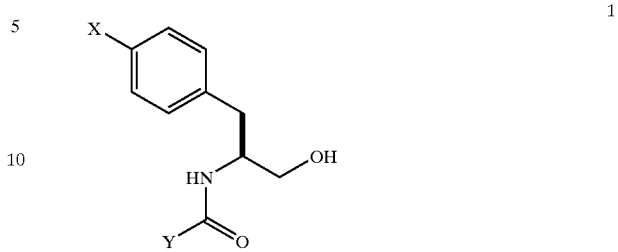

1 and the pharmaceutically acceptable salts and esters thereof wherein X and Y are as defined below, are more readily absorbed and more bioavailable than the corresponding carboxylic acids from which they are derived, both of which are effective inhibitors of the binding of VCAM-1 to VLA-4 in vivo and are useful in treating inflammation in inflammatory diseases in which such binding acts to bring on the inflammation.

DETAILED DESCRIPTION OF THE INVENTION

The present invention comprises alcohols of the formula:

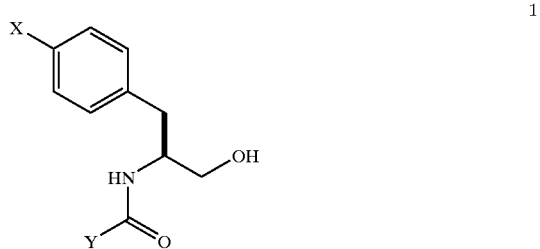

1 wherein:
in accordance with the invention, X is a group X-1, X-2 or X-3 as described below. Y is a group Y-1, Y-2 or Y-3 as described below.

The group X-1 is of the formula:

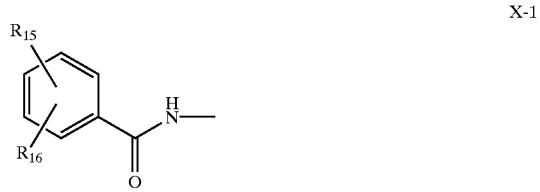

X-1 wherein:
$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aroyl, aryl, aryloxy;
$R_{16}$ is hydrogen, halogen, nitro, cyano, lower alkyl, OH, perfluorolower alkyl, or lower alkylthio.

The groups $R_{15}$ is preferably lower alkyl, nitro, halogen (especially chloro or fluoro), perfluoromethyl, or cyano and $R_{16}$ is preferably independently hydrogen, lower alkyl, nitro, halogen (especially chloro or fluoro), perfluoromethyl, or cyano.

X-2 is a group of the formula:

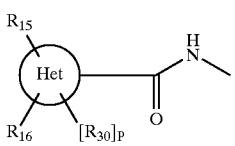

wherein Het is a 5- or 6-membered heteroaromatic ring containing 1, 2 or 3 heteroatoms selected from N,O, and S, or
Het is a 9- or 10-membered bicyclic heteroaromatic ring containing 1, 2, 3 or 4 heteroatoms selected from O, S, and N;
$R_{15}$ and $R_{16}$ are as above, and
$R_{30}$ is hydrogen or lower alkyl, p is an integer from 0 to 1;

Het is preferably a 5- or 6-membered monocyclic heteroaromatic ring containing 1, 2 or 3 nitrogens, or a nitrogen and a sulfur, or a nitrogen and an oxygen. When Het is a bicyclic heteroaromatic ring, it preferably contains from 1 to 3 nitrogens as the heteroatoms. Where X is X-2, $R_{15}$ is preferably, nitro, lower alkyl sulfonyl, cyano, lower alkyl, lower alkoxy, perfluorolower alkyl, lower alkylthio, lower alkanoyl, or aryl (especially unsubstituted phenyl); $R_{16}$ is preferably hydrogen, halogen, nitro, cyano, lower alkyl, perfluoro lower alkyl; and $R_{30}$, when present, is preferably hydrogen or lower alkyl.

The group X-3 is of the formula:

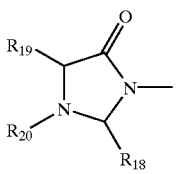

wherein:
$R_{18}$ is aryl, heteroaryl,
$R_{19}$ is substituted or unsubstituted lower alkyl, aryl, heteroaryl, arylalkyl, heteroaryl alkyl, and
$R_{20}$ is substituted or unsubstituted lower alkanoyl or aroyl
$R_{18}$ is preferably phenyl. $R_{19}$ is preferably lower alkyl, which is unsubstituted or substituted by pyridyl or phenyl. $R_{20}$ is preferably lower alkanoyl
Y is a group of formula Y-1, Y-2, or Y-3 wherein:
Y-1 is a group of the formula:

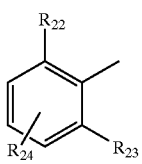

wherein:
$R_{22}$ and $R_{23}$ are independently hydrogen, lower alkyl, lower alkoxy, lower cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and
$R_{24}$ is hydrogen, lower alkyl, lower alkoxy, aryl, nitro, cyano, lower alkyl sulfonyl, or halogen.
Y-2 is a five or six membered heteroaromatic ring bonded via a carbon atom to the amide carbonyl wherein said ring contains one, two or three heteroatoms selected from the group consisting of N, O, and S and one or two atoms of said ring are independently substituted by lower alkyl, cycloalkyl, halogen, cyano, perfluoroalkyl, or aryl and at least one of said substituted atom is adjacent to the carbon atom bonded to the amide carbonyl.

Y-3 is a 3–7 membered ring of the formula:

wherein:
$R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$; $R_{28}$ is H or lower alkyl;

$R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl, 5or $R_{28}$ and $R_{29}$ taken together form a 4, 5 or 6-membered saturated carbocyclic ring optionally containing one hetero atom selected from O, S, and N; the carbon atoms in the ring being unsubstituted or substituted by lower alkyl or halogen;

Q is —$(CH_2)_fO$—, —$(CH_2)_fS$—, —$(CH_2)_fN(R_{27})$—, or —$(CH_2)_f$—;

$R_{27}$ is H, lower alkyl, aryl, lower alkanoyl, aroyl or lower alkoxycarbonyl;

e is an integer from 0 to 4; f is an integer from 0 to 3; and the dotted bond can be optionally hydrogenated.

These compounds are useful as anti inflammatory agents in treating inflammatory diseases These alcohols of Formula 1 are more effective inhibitors of the VCAM-VLA- 4 interaction and anti-inflammatory agents in vivo than the corresponding acids and esters form which they are derived. They are more bioavailable than these corresponding acids and esters from which are derived. It has been found that the compounds of this invention are more readily orally adsorbed than the acids or esters from which they are derived.

Therefore, this invention is directed to compounds of formula 1

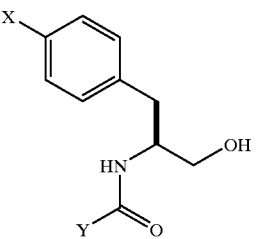

wherein:

X is selected from the group of the formula:

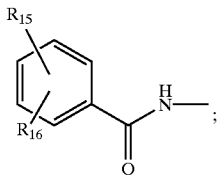
X-1

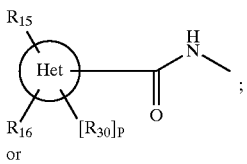
X-2 or

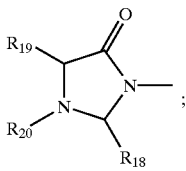
X-3

$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aroyl, aryl, aryloxy;

$R_{16}$ is hydrogen, halogen, nitro, cyano, lower alkyl, OH, perfluorolower alkyl, or lower alkylthio; Het is a 5- or 6-membered heteroaromatic ring containing 1, 2 or 3 heteroatoms which are N,O, or S, or is a 9- or 10-membered bicyclic heteroaromatic ring containing 1, 2, 3 or 4 heteroatoms which are O, S, or N; $R_{30}$ is hydrogen or lower alkyl; p is an integer from 0 to 1; $R_{18}$ is aryl, heteroaryl;

$R_{19}$ is substituted or unsubstituted lower alkyl, aryl, heteroaryl, arylalkyl, heteroaryl alkyl, and $R_{20}$ is substituted or unsubstituted lower alkanoyl or aroyl; Y is selected from the group consisting of a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl; a phenyl moiety of the formula:

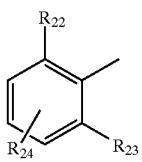
Y-1 or a three to seven membered ring of the formula:

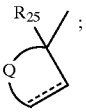
Y-3

$R_{22}$ and $R_{23}$ are independently hydrogen, lower alkyl, lower alkoxy, lower cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen;

$R_{24}$ is hydrogen, lower alkyl, lower alkoxy, aryl, nitro, cyano, lower alkyl sulfonyl, or halogen;

$R_{25}$ is lower alkyl, unsubstituted or fluorine substituted lower alkenyl, or $R_{26}$—$(CH_2)_e$—;

$R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$; $R_{28}$ is H or lower alkyl; $R_{29}$ is hydrogen, lower alkyl; lower alkoxycarbonyl, lower alkanoyl, aroyl, perfluoro lower alkanoylamino, lower alkyl sulfonyl, lower alkylaminocarbonyl, arylaminocarbonyl, or $R_{28}$ and $R_{29}$ taken together form a 4, 5 or 6-membered saturated carbocyclic ring optionally containing one heteroatom selected from O, S, and N; with the carbon atoms in the ring being unsubstituted or substituted by lower alkyl or halogen;

Q is —$(CH_2)_fO$—, —$(CH_2)_fS$—, —$(CH_2)_fN(R_{27})$—, —$(CH_2)_f$—;

$R_{27}$ is H, lower alkyl, aryl, lower alkanoyl, aroyl or lower alkoxycarbonyl;

e is an integer from 0 to 4; f is an integer from 0 to 3; and the dotted bond can be optionally hydrogenated.

Preferred compounds are as follows:

A compound of formula 1 wherein X is a group of the formula X-1 and $R_{15}$ and $R_{16}$ are as in claim 1, preferably where $R_{15}$ is lower alkyl, nitro, halogen, perfluoromethyl, or cyano and $R_{16}$ is independently hydrogen, lower alkyl, nitro, halogen, perfluoromethyl, or cyano, and particularly where $R_{15}$ and $R_{16}$ are independently chloro or fluoro, and/or where X is selected from the group of

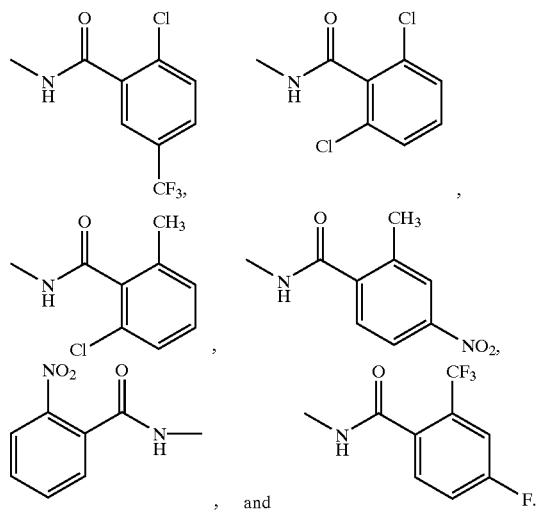

A compound of formula 1 wherein X is a group of the formula X-2 and p, and $R_{15}$, $R_{16}$, and $R_{30}$ are as in formula 1 (compound A), especially where Het is a 5- or 6-membered monocyclic heteroaromatic ring containing 1, 2 or 3 nitrogens, or a nitrogen and a sulfur, or a nitrogen and an oxygen, or where Het is a bicyclic heteroaromatic ring containing from 1 to 3 nitrogens, or where $R_{15}$ is nitro, lower alkyl sulfonyl, cyano, lower alkyl, lower alkoxy, perfluorolower alkyl, lower alkylthio, lower alkanoyl, or aryl, especially unsubstituted phenyl.

Compound A preferably where $R_{16}$ is hydrogen, halogen, nitro, cyano, lower alkyl, perfluoro lower alkyl; and $R_{30}$ is hydrogen or lower alkyl.

Compound A preferably where Het is a 6 membered monocyclic heteroaromatic ring containing 1 or 2 nitrogens or a 10 membered bicyclic heteroaromatic ring containing one nitrogen, $R_{15}$ is lower alkyl, or perfluoroalkyl and $R_6$ is independently hydrogen, lower alkyl, or perfluoroalkyl, and $R_{30}$ is absent.

Compound A preferably where X is selected from the group of

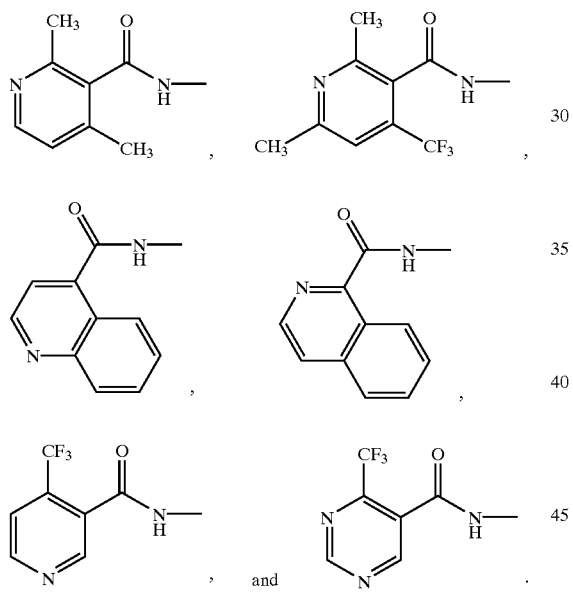

A compound of formula 1 wherein X is X-3 and $R_{18}$, $R_{19}$, and $R_{20}$ are as in formula 1, especially where $R_{18}$ is phenyl, or $R_{19}$ is lower alkyl which is unsubstituted or substituted by pyridyl or phenyl, or $R_{20}$ is substituted or unsubstituted lower alkanoy, or $R_{18}$ is phenyl, $R_{19}$ is lower alkyl which is unsubstituted or substituted by pyridyl or phenyl and $R_{20}$ is lower alkanoyl, or $R_{18}$ is phenyl which is unsubstituted or substituted by halogen or lower alkoxy; $R_{19}$ is phenyl lower alkyl which is unsubstituted or substituted by lower alkoxy, pyridyl lower alkyl, or lower alkyl; and $R_{20}$ is substituted or unsubstituted lower alkanoyl. In the last compound, preferably X is selected from the group of

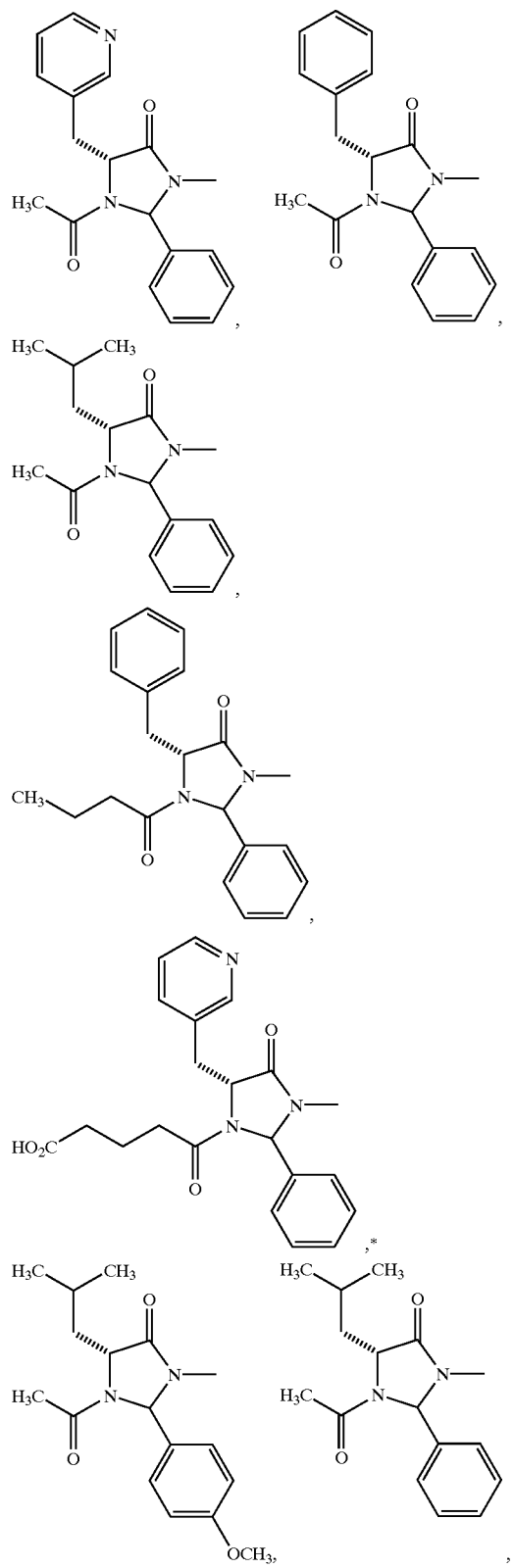

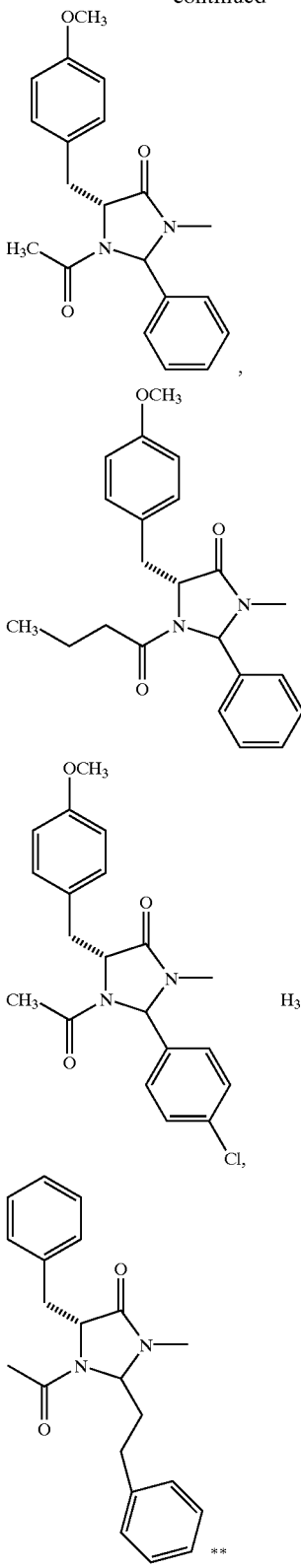

A compound of formula 1 wherein Y is Y-1 and $R_{22}$, $R_{23}$, and $R_{24}$ are as in claim 1, especially where $R_{22}$ and $R_{23}$ are lower alkyl, trifluoromethyl, or halogen and $R_{24}$ is hydrogen, lower alkyl, lower alkoxy, or halogen, and preferably where Y-1 is selected from the group of

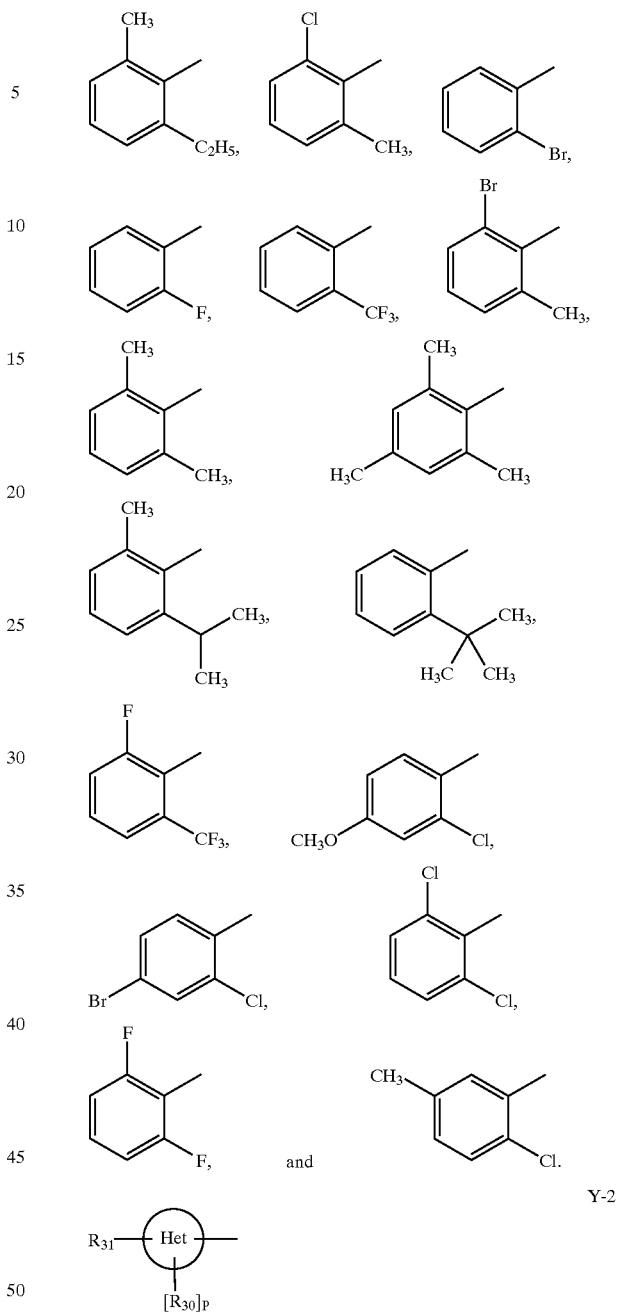

A compound of formula 1 wherein Y is Y-2 and p, Het, R30 and R31, are as in formula 1, especially where Het is a 6 membered heteroaromatic ring, preferably where the heteroatom is N, and most preferably where Y-2 is selected from the group of

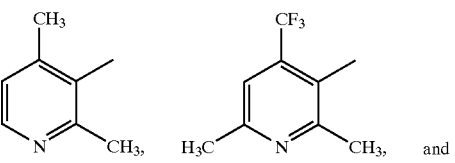

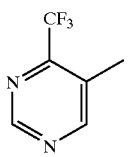
A compound of formula 1 wherein Y is a group of formula Y-3 and Y, $R_{25}$ and Q are as in claim 1; e is an integer from 0 to 4; f is an integer from 0 to 3; and the dotted bond can be optionally hydrogenated, especially where Y is selected from the group of the formula:
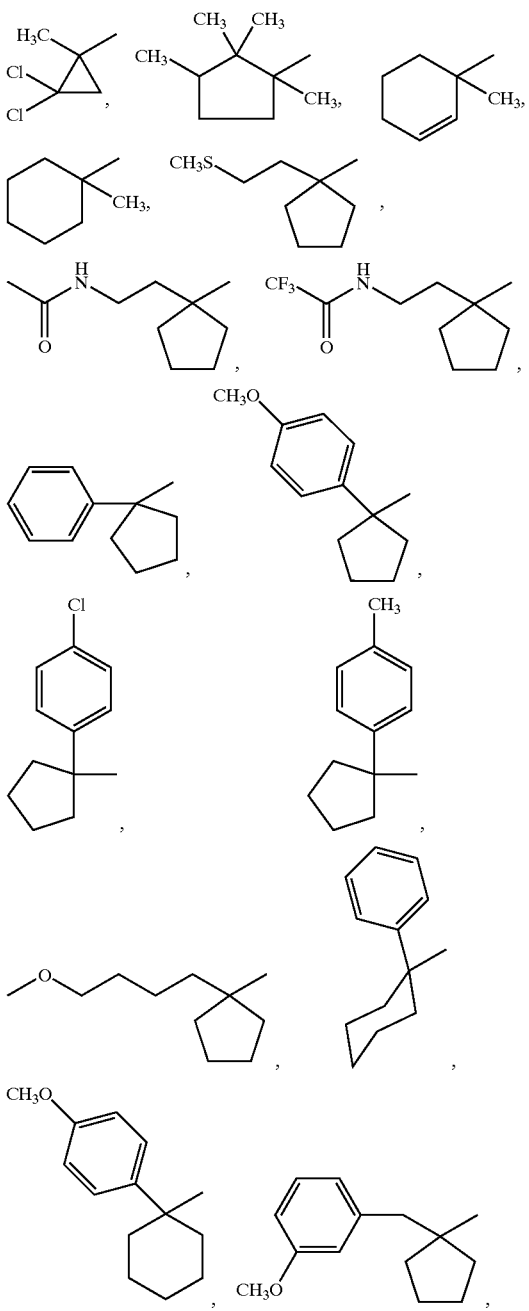
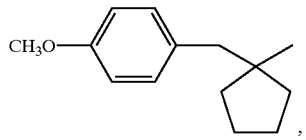
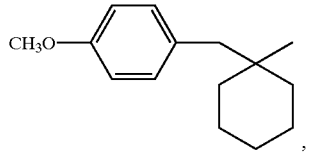
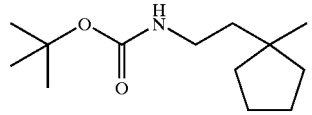
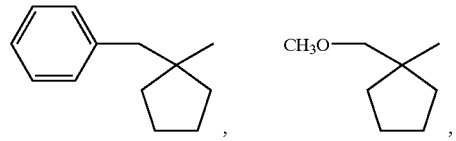
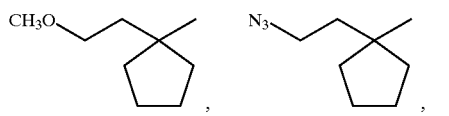
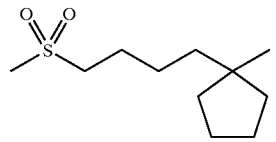
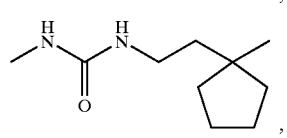
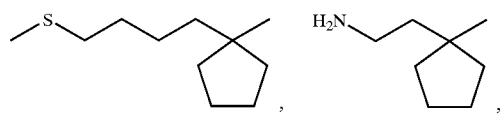
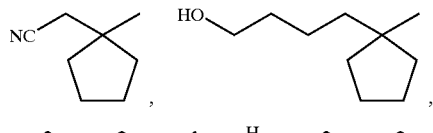
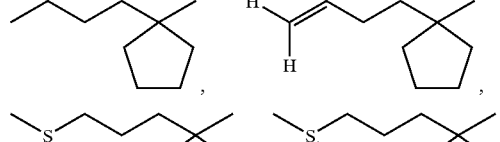
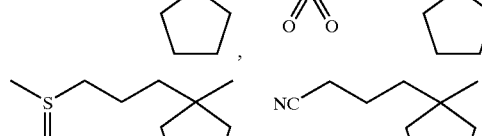
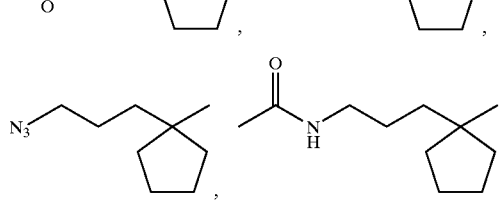

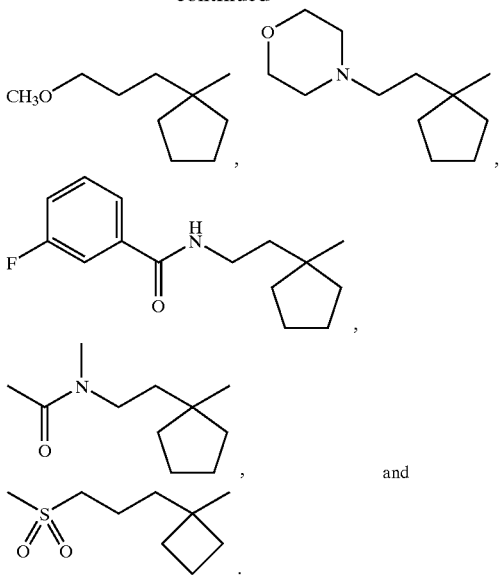

A compound of formula 1 wherein X is a group of the formula X-1 where $R_{15}$ and $R_{16}$ are as above and Y is a group of the formula Y-1 where $R_{22}$, $R_{23}$ and $R_{24}$ are as above.

A compound of formula 1 wherein X is a group of the formula X-1 wherein $R_{15}$ and $R_{16}$ are as above and Y is Y-3.

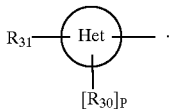

Y-2

A compound of formula 1 wherein X is X-1 wherein $R_{15}$ and $R_{16}$ are as above and Y is a group of the formula Y-3 wherein $R_{25}$ and Q are as above; e is an integer from 0 to 4; f is an integer from 1 to 3; and the dotted bond can be optionally hydrogenated (compound B).

A compound of formula 1 wherein X is X-2 and Y is Y-1.
A compound of formula 1 wherein X is X-2 and Y is Y-2.
A compound of formula 1 wherein X is X-2 and Y is Y-3, $_{15}$, $R_{16}$, $R_{25}$, $R_{30}$, and p

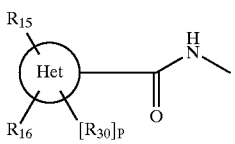

X-2 are as above; e is an integer from 0 to 4; f is an integer from 0 to 3; and the dotted bond can be optionally hydrogenated.

A compound of formula 1 wherein X is X-3 and Y is Y-1.
A compound of formula 1 wherein X is X-3 and Y is Y-2.
A compound of formula 1 wherein X is X-3 and Y is Y-3.
A compound of formula 1 wherein X is X-1 and $R_{16}$ is hydrogen, lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl, and Y is a group of the formula Y-1 where $R_{22}$ is hydrogen, halogen, trifluoroalkyl, or lower alkyl and $R_{23}$ is halogen, trifluoroalkyl, or lower alkyl, and $R_{24}$ is hydrogen or Y is a group of the formula Y-3 which is a four to six membered cycloalkyl ring, $R_{25}$ is $R_{26}$—(CH2)e—; e is 2–4 and $R_{26}$ is azido, cyano, hydroxy, lower alkoxy, lower alkoxycarbonyl, lower alkanoyl, lower alkyl sulfonyl, lower alkyl sulfinyl, perfluoro lower alkanoyl, nitro, or lower alkylthio or $R_{25}$ is $NHR_{29}$ where $R_{29}$ is lower alkanoyl or lower alkylamino carbonyl; and the dotted bond is hydrogenated (compound C).

Preferably X is a group of the formula X-1 and $R_{16}$ is hydrogen, lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl; and Y is Y-1 where $R_{22}$ is hydrogen, halogen, or lower alkyl and $R_{23}$ is halogen or lower alkyl, and $R_{24}$ is hydrogen. It is more preferred that $R_{16}$ is hydrogen or halogen and $R_{15}$ is halogen; $R_{22}$ is hydrogen, halogen, ethyl, or methyl and $R_{23}$ is halogen, ethyl, or methyl, or that $R_{15}$ is lower alkyl or halogen and $R_{16}$ is hydrogen, lower alkyl, halogen and $R_{22}$ and $R_{23}$ is ethyl or lower alkyl or halogen. Examples of such compounds are 4-[[(2,6-dichloro-phenyl)carbonyl]amino]-N-[(2-chloro-6-methylphenyl)carbonyl]-L-phenylalaninol and 4-[[(2,6-dichloro-phenyl)carbonyl]amino]-N-[(2-bromophenyl)carbonyl]-L-phenylalanine alcohol.

Compound B is preferred where $R_{15}$ is halo, perfluoro lower alkyl, nitro, lower alkyl, and $R_{16}$ is hydrogen halo, perfluoro lower alkyl, nitro, lower alkyl and Y is a five or six membered cycloalkyl ring of the formula

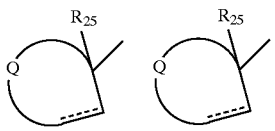

with Q being —(CH$_2$)$_f$ and f being, 1 and 2; $R_{25}$ being $R_{26}$—(CH$_2$)$_e$—; e being a integer of 0 to 4, and $R_{26}$ being lower alkyl, hydroxy, lower alkoxy, lower alkyl thio, or lower alkyl sulfonyl; and the dotted bond is hydrogenated. Examples of such compounds are 4-[[(2-methyl-5-nitrophenyl)carbonyl]amino]-N-[[1-[4-(methylsulfonyl)butyl]cyclopentyl]carbonyl]-L-phenylalanine alcohol.

4-[[(2,6-dimethylphenyl)carbonyl]amino]-N-[[1-[4-(methylsulfonyl)butyl]cyclopentyl]carbonyl]-L-phenylalanine alcohol.

4-[[(2-trifluoro-methylphenyl) carbonyl]amino]-N-[[1-[4-(methylsulfonyl)butyl]cyclopentyl]carbonyl]-L-phenylalanine alcohol 4-[[(2-methyl-5-nitrophenyl)carbonyl]amino]-N-[[1-[4-(methylthio)butyl]cyclopentyl]carbonyl]-L-phenylalanine alcohol 4-[[(2,6-dichlorophenyl)carbonyl]amino]-N-[[1-[3-(methylsulfonyl)propyl]cyclopentyl]carbonyl]-L-phenylalanine alcohol.

4-[[(2,6-dichlorophenyl) carbonyl]amino]-N-[[1-(2-methoxyethyl)cyclopentyl]carbonyl]-L-phenylalanine alcohol 4-[[(2,6-dichlorophenyl)carbonyl]amino]-N-[[1-[4-[methylsulfonyl)butyl]cyclopentyl]-L-phenylalanine alcohol.

Compound C is preferred where Y is Y-1 and $R_{22}$ is hydrogen, halogen, or lower alkyl and $R_{23}$ is halogen, or lower alkyl and $R_{24}$ is hydrogen, especially where $R_{15}$, and $R_{16}$ are hydrogen, lower alkyl or halogen. Examples of such compounds are 4-[[(2,6-dichloro-phenyl)carbonyl]amino]-N-[(2-bromophenyl)carbonyl]-L-phenylalanine alcohol and 4-[[(2,6-dimethylphenyl)carbonyl]amino]-N-[(2-bromophenyl)carbonyl]-L-phenylalanine alcohol.

The alcohol compounds of formula 1 are derived from the corresponding acid and esters

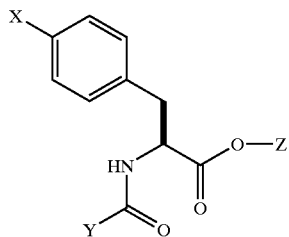

2 wherein X and Y are as above and 2 is lower alkyl or hydrogen.

The preparation of compounds of formula 2 are described in Chen, et al. Ser. No. 09/138,353 filed Aug. 21, 1998 and Ser. No. 09/137,798 filed Aug. 21, 1998. The disclosures of which are incorporated by reference. The compounds of formula 2 where Y is Y-1 and Y-2 are disclosed in said Ser. No. 09/137,798 filed Aug. 21, 1998, Chen et al. as well as their method of preparation. The compound where Y is in formula 2 is Y-3 and their method of preparation are disclosed in Ser. No. 09/138,353 filed Aug. 21, 1998. These alcohols of formula 1 and esters of formula 2 are useful in treating inflammation diseases involving inflammation caused by the binding of VLA-4 to VCAM-1 binding such as rheumatoid arthritis, multiple sclerosis, pulmonary arthritis (e.g. asthma and inflammatory bowel diseases.

As used in this specification, the term "lower alkyl", alone or in combination, means a straight--chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Lower alkyl groups may be subsituted by one or more groups selected independently from cycloalkyl, nitro, aryloxy, aryl, hydroxy, halogen, cyano, lower alkoxy, lower alkanoyl, lower alkylthio, lower alkyl sulfinyl, lower alkyl sulfonyl, and substituted amino. Examples of substituted lower alkyl groups include 2-hydroxyethyl, 3-oxobutyl, cyanomethyl, and 2-nitropropyl The term "lower alkenyl" means a nonaromatic partially unsaturated hydrocarbon chain containing at least one double bond, which is preferably 1–10 and more preferably 1–6 carbons in length. The group may be unsubstituted or substituted with conventional substituents, preferably fluoro. Examples are vinyl, allyl, dimethylallyl, butenyl, isobutenyl, and pentenyl.

The term "cycloalkyl" means an unsubstituted or substituted 3- to 7-membered carbacyclic ring. Substitutents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino.

The term "lower alkoxy" means a straight-chain or branched-chain alkoxy group containing a maximum of six carbon atoms, such as methoxy, ethoxy, n-propoxy, isopropoxy, n-butoxy, tert-butoxy and the like.

The term "lower alkylthio" means a lower alkyl group bonded through a divalent sulfur atom, for example, a methyl mercapto or a isopropyl mercapto group.

The term "aryl" means a mono- or bicylic aromatic group, such as phenyl or naphthyl, which is unsubstituted or substituted by conventional substituent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanoyl, aroyl, aryl alkynyl, lower alkynyl and lower alkanoylamino. Examples of aryl groups that may be used in accordance with this invention are p-tolyl, p-methoxyphenyl, p-chlorophenyl, m-methylthiophenyl, 2-methyl-5-nitrophenyl, 2,6-dichlorophenyl, 1-naphthyl and the like.

The term "arylalkyl" means a lower alkyl group as hereinbefore defined in which one or more hydrogen atoms is/are replaced by an aryl or heteroaryl group as herein defined. Any conventional arylalkyl may be used in accordance with this invention, such as benzyl and the like.

The term "heteroaryl" means an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of hetereoaryl rings are pyridine, benzimidazole, indole, imidazole, thiophene, isoquinoline, quinazoline and the like. Substitutents as defined above for "aryl" are included in the definition of heteroaryl.

The term "lower alkoxycarbonyl" means a lower alkoxy group bonded via a carbonyl group. Examples of alkoxycarbonyl groups are ethoxycarbonyl and the like.

The term "lower alkylcarbonyloxy" means lower alkyl-carbonyloxy groups bonded via an oxygen atom, for example an acetoxy group.

The term "lower alkanoyl" means lower alkyl groups bonded via a carbonyl group and embraces in the sense of the foregoing definition groups such as acetyl, propionyl and the like.

The term "lower alkylcarbonylamino" means lower alkylcarbonyl groups bonded via a nitrogen atom, such as acetylamino.

The term "aroyl" means an mono- or bicyclic aryl or heteroaryl group bonded via a carbonyl group. Examples of aroyl groups are benzoyl, 3-cyanobenzoyl, 2-naphthoyl and the like.

In the group Y-1, $R_{22}$ and $R_{23}$ are preferably lower alkyl or halogen and R24 is preferably hydrogen.

Among the groups Y-1, when $R_{23}$ is lower-alkyl or halogen, Y-1 is preferably:

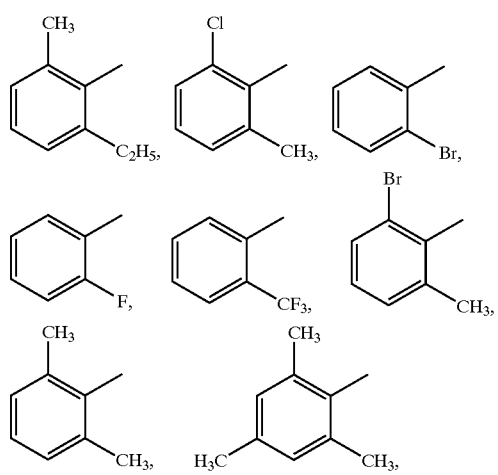

-continued
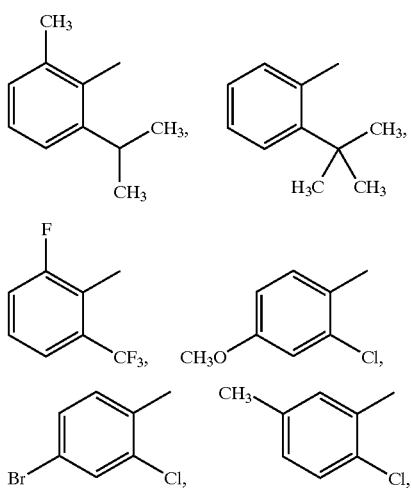
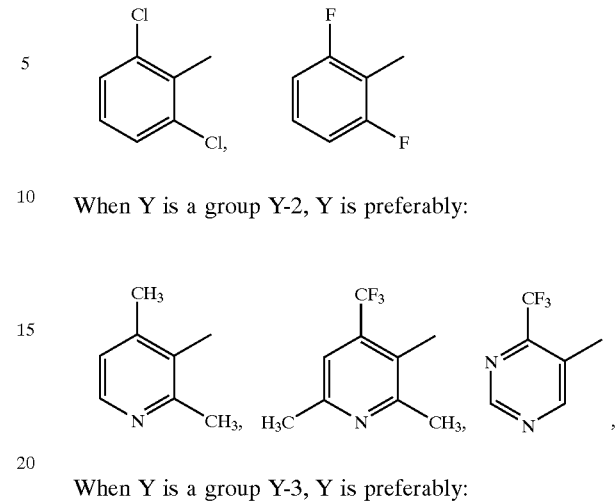
When Y is a group Y-2, Y is preferably:
When Y is a group Y-3, Y is preferably:
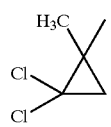 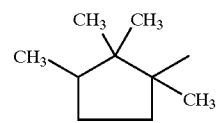 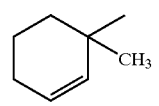
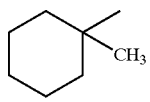 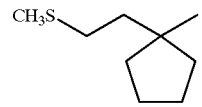 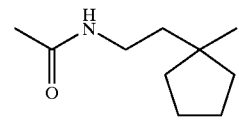
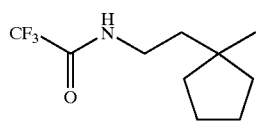 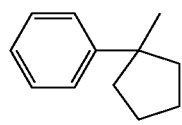 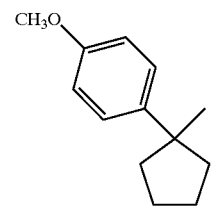
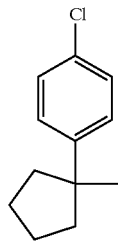 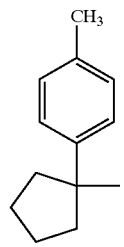 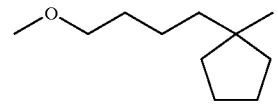
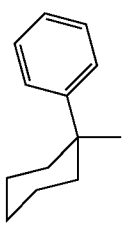 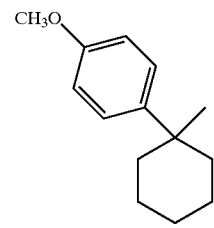 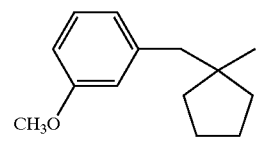

-continued
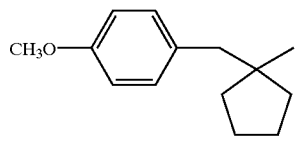 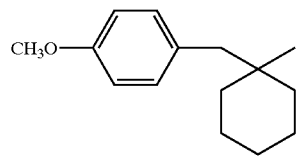 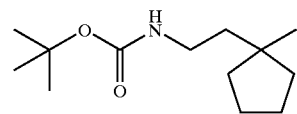
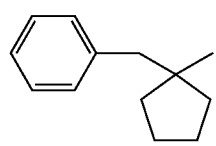 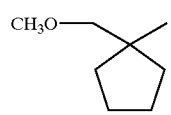 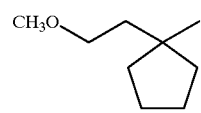
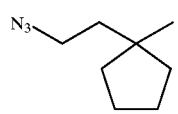 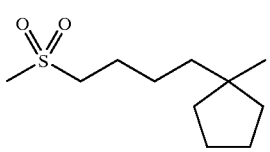 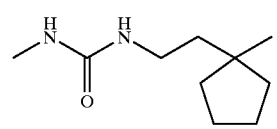
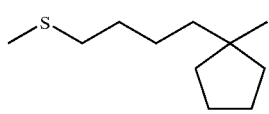 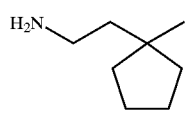 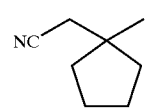
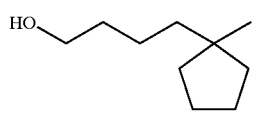 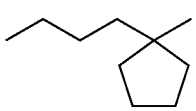 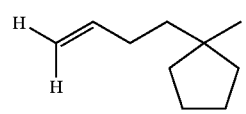
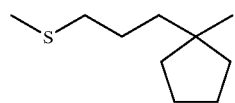 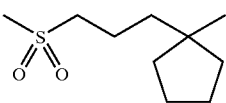 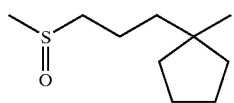
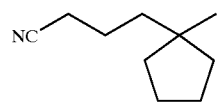 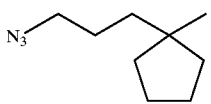 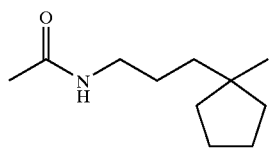
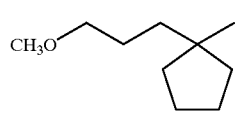 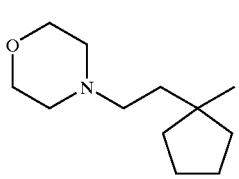 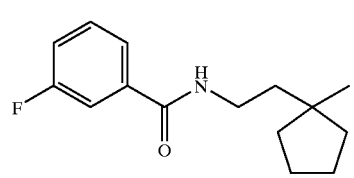
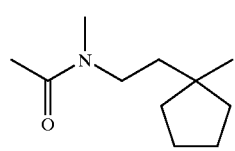 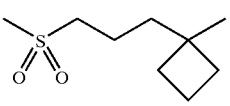

The especially preferred groups X-1 are of the formula:
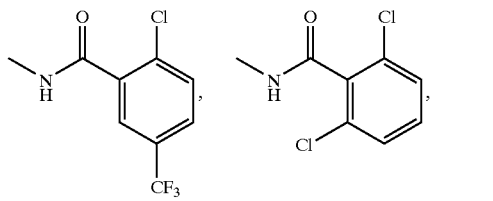
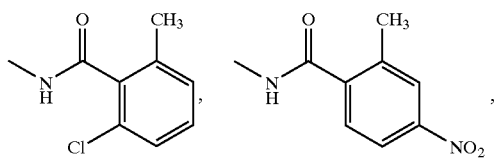
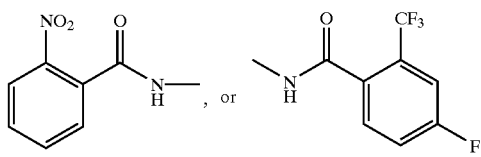, or 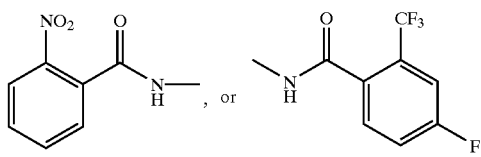
The especially preferred groups X-2 are of the formula:
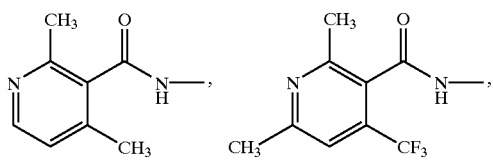
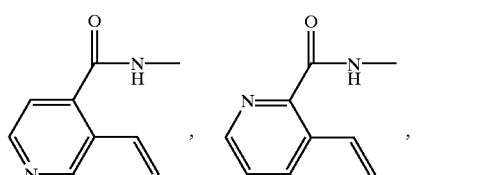
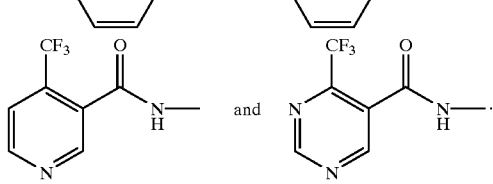 and
The especially preferred groups X-3 are of the formula:
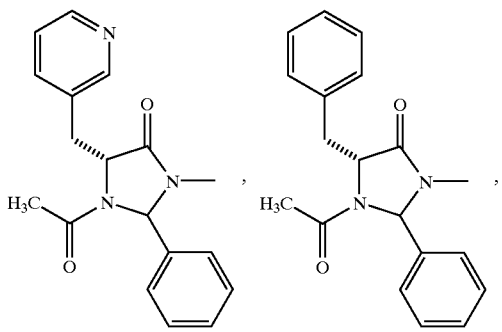
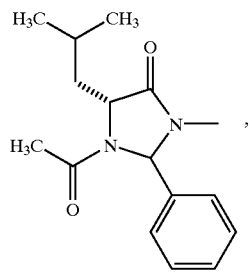
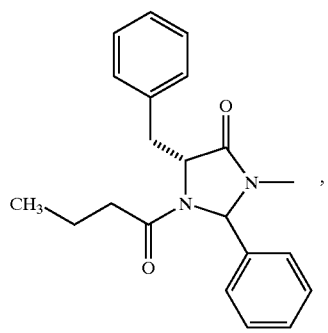
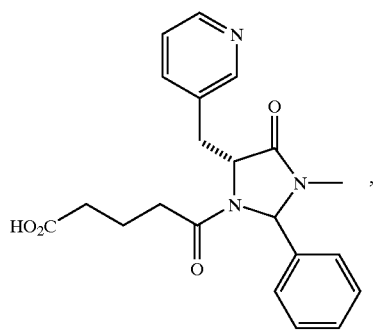
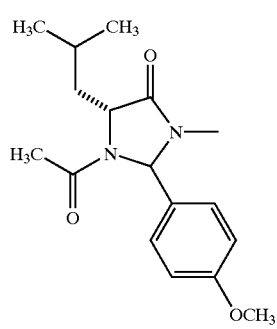
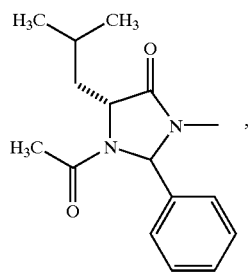

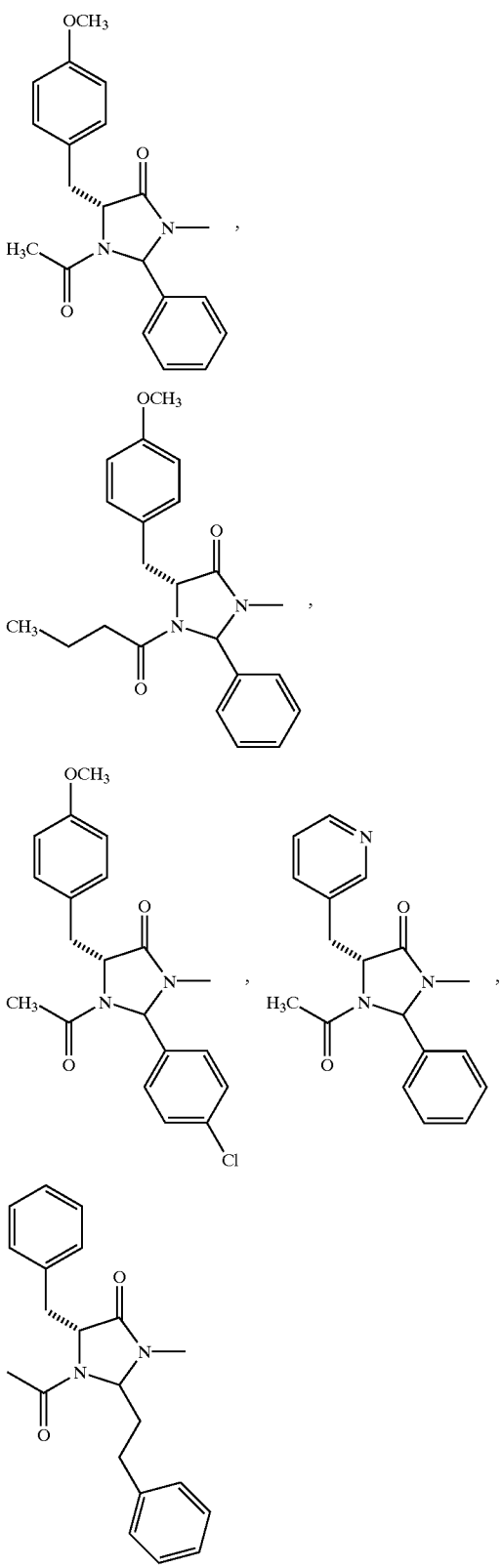

Y is preferably the group Y-1 whereby the invention comprises a compound of the formula:

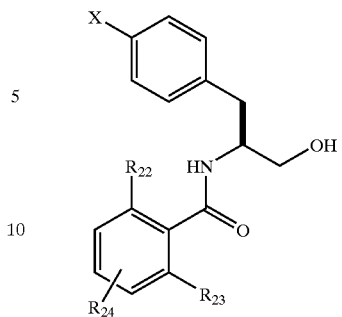

wherein X, $R_{22}$, $R_{23}$ and $R_{24}$ are as above.

In the group Y-1, $R_{22}$ and $R_{23}$ are preferably lower alkyl or halogen and $R_{24}$ is preferably hydrogen.

The more preferred groups X is X-1 when X is X-1, $R_5$ is more preferably halogen, nitro, lower alkyl sulfonyl, cyano, lower alkyl, lower alkoxy, perfluorolower alkyl, lower alkylthio, alkylsulfinyl lower alkyl, alkylsufonyl lower alkyl, lower alkylsulfinyl, lower alkanoyl, or aroyl. $R_{16}$ is more preferably H, halogen, nitro, cyano, lower alkyl, perfluorolower alkyl, or lower alkylthio.

Most preferred is the structure of the formula:

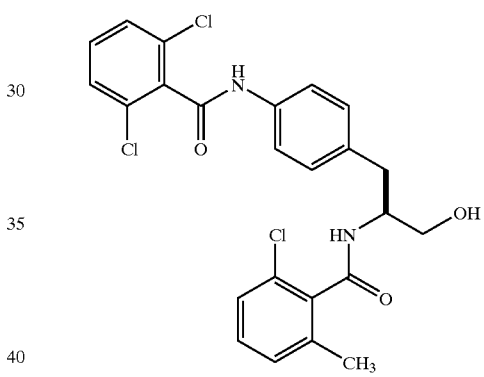

The compounds of the invention can exist as stereoisomers and diastereomers, all of which are encompassed within the scope of the present invention.

The compounds and their metabolites of the invention inhibit the binding of VCAM-1 and fibronectin to VLA-4 on circulating lymphocytes, eosinophils, basophils, and monocytes ("VLA-4-expressing cells"). The binding of VCAM-1 and fibronectin to VLA-4 on such cells is known to be implicated in certain disease states, such as rheumatoid arthritis, multiple sclerosis, inflammatory bowel disease, and particularly in the binding of eosinophils to pulmonary endothelium which is the cause of the pulmonary inflammation which occurs in asthma. Thus, the compounds of the present invention would be useful for the treatment of asthma.

On the basis of their capability to inhibit the binding of VCAM-1 and fibronectin to VLA-4 on circulating lymphocytes, eosinophils, basophils, and monocytes, the compounds and their metabolites of the invention can be used as medicaments for the treatment of disorders which are known to be associated with such binding. Examples of such disorders are rheumatoid arthritis, multiple sclerosis, asthma, and inflammatory bowel disease. The compounds of the invention are preferably used in the treatment of diseases which involve pulmonary inflammation, such as asthma.

The pulmonary inflammation which occurs in asthma is related to eosinophil infiltration into the lungs wherein the eosinophils bind to endothelium which has been activated by some asthma-triggering event or substance.

Furthermore, acylphenylalanine derivatives metabolically derived from compounds of the invention also inhibit the binding of VCAM-1 and MadCAM to the cellular receptor alpha4-beta7, also known as LPAM, which is expressed on lymphocytes, eosinophiles and T-cells. While the precise role of alpha4-beta7 interaction with various ligands in inflammatory conditions such as asthma is not completely understood, compounds of the invention which inhibit both alpha4-beta1 and alpha4-beta7 receptor binding are particularly effective in animal models of asthma. Furthermore work with monoclonal antibodies to alpha4-beta7 indicate that compounds which inhibit alpha4-beta7 binding to Mad-CAM or VCAM are useful for the treatment of inflammatory bowel disease. They would also be useful in the treatment of other diseases in which such binding is implicated as a cause of disease damage or symptoms.

The compounds of the invention can be administered orally, rectally, or parentally, e.g., intravenously, intramuscularly, subcutaneously, intrathecally or transdermally; or sublingually, or as opthalmalogical preparations, or as an aerosol in the case of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of use. The dosages in which the compounds of the invention are administered in effective amounts depending on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 of fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being especially preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of the invention.

The compounds of the present invention may be prepared by any conventional means. In reaction Scheme 1, a compound of formula 2 in which Z is lower alkyl, and which is a known compound prepared as described in Ser. No. 09/138,353 and 09/137,798 is treated with a reducing agent capable of selectively reducing a carbocyclic ester. For example treatment with a compound of formula 2 with an alkali borohydride, such as sodium borohydride in alcohol solution at about room temperature smoothly effects reduction to give a compound of formula 1. The method of preparation for the compounds of formula 2 are disclosed in Ser. Nos. 09/138,353 and 09/137,798 is hereby incorporated by reference.

Scheme 1 wherein X and Y are as above.

General Melting points were taken on a Thomas-Hoover apparatus and are uncorrected. Optical rotations were determined with a Perkin-Elmer model 241 polarimeter. $^1$H-NMR spectra were recorded with Varian XL-200 and Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230–400 mesh silica gel for flash chromatography; columns were run under a 0–5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to $I_2$ vapor, or by spaying with either phosphomolybdic acid (PMA) in aqueous ethanol, or after exposure to $Cl_2$, with a 4,4'-tetramethyldiaminodiphenylmethane reagent prepared according to E. Von Arx, M. Faupel and M Brugger, *J. Chromatography*, 1976, 120, 224–228.

Reversed phase high pressure liquid chromatography (RP-HPLC)was carried out using either a Waters Delta Prep 4000 employing a 3×30 cm, Waters Delta Pak 15 μM C-18 column at a flow of 40 mL/min employing a gradient of acetonitrile:water (each containing 0.75% TFA) typically from 5 tp 95% acetonitrile over 35–40 min or a Rainin HPLC employing a 41.4 mmx30 cm, 8 μM, Dynamax$^{TM}$C-18 column at a flow of 49 mL/min and a similar gradient of acetonitrile:water as noted above.

Dichloromethane ($CH_2Cl_2$), 2-propanol, DMF, THF, toluene, hexane, ether, and methanol, were Fisher reagent grade and were used without additional purification except as noted, acetonitrile was Fisher hplc grade and was used as is.

Definitions:
THF is tetrahydrofuran,
DMF is N,N-dimethylformamide,
HOBT is 1-hydroxybenzotriazole,
BOP is [(benzotriazole-1-yl)oxy]tris-(dimethylamino) phosphonium hexafluorophosphate, HATU is O-(7-azabenzotriazol-1-yl)-1,1,3,3-tetramethyluronium hexafluorophosphate HBTU is O-benzotriazole-N,N,N',N',-tetramethyluronium hexafluorophosphate, DIPEA is diisopropylethylamine, DMAP is 4-(N,N-dimethylamino)pyridine DPPA is diphenylphosphoryl azide DBU is 1,8-diazabicyclo[5.4.0]undec-7-ene NaH is sodium hydride brine is saturated aqueous sodium chloride solution TLC is thin layer chromatography LDA is lithium diisopropylamide BOP-Cl is bis(2-oxo-3-oxazolidinyl)phosphinic chloride NMP is N-methyl pyrrolidinone

EXAMPLES

Example 1.

Synthesis of 4-[[(2,6-dichlorophenyl)carbonyl]amino]-N-[(2-chloro-6-methylphenyl)carbonyl]-L-phenylalaninol.

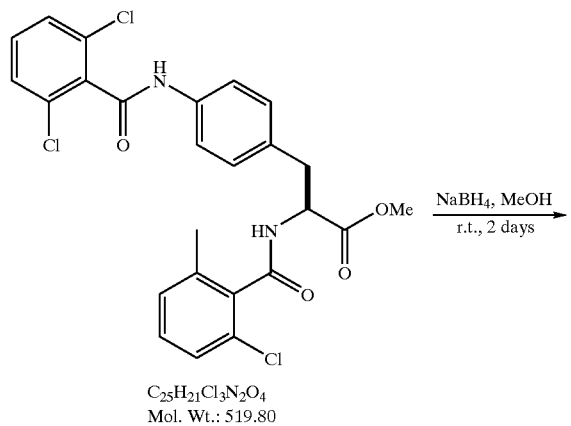

$C_{25}H_{21}Cl_3N_2O_4$
Mol. Wt.: 519.80

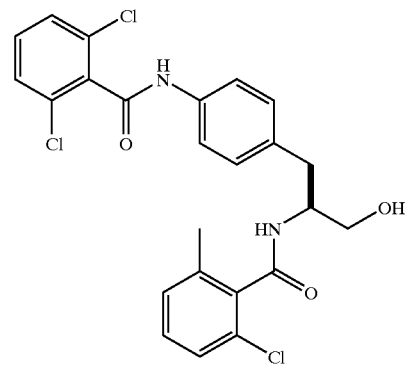

$C_{24}H_{21}Cl_3N_2O_3$
Mol. Wt.: 491.79

To a solution of 4-[[(2,6-dichlorophenyl)carbonyl]amino]-N-[(2-chloro-6-methylphenyl) carbonyl]-L-phenylalanine methyl ester (9.9 mmol, 5.14 g) in methanol (55 mL) was added excess sodium borohydride (198 mmol, 7.49 g) in six portions during a period of 8 h at room temperature. The slow addition of sodium borohydride is crucial to control an exothermic reaction and evolution of gas with foaming. After addition, the resulting solution was stirred for 2 days at room temperature, at which time the TLC analysis of the mixture indicated the absence of starting material. The excess hydride was destroyed by a slow addition of water (20 mL). The methanol was removed under vacuum and the resulting solid was dissolved in a mixture of water (30 mL), saturated ammonium chloride (80 mL) and ethyl acetate (150 mL). The two layers were separated and the aqueous layer was extracted with ethyl acetate (70 mL). The combined extracts were washed with brine solution (100 mL) and dried over anhydrous magnesium sulfate. After filtration of the drying agent, the filtrate was concentrated under vacuum to give 5.3 g of crude compound which was purified by a silica gel column chromatography, eluting with ethyl acetate and hexane (3:1) to afford 4.5 g (92%) of 4-[[(2,6-dichlorophenyl)carbonyl]amino]-N-[(2-chloro- 6-methylphenyl)carbonyl]-L-phenylalanine alcohol as a white solid: mp 198–200° C. HR MS: Obs.mass, 491.0699. Calcd. mass, 491.0696 (M+H).

Example 2.

Synthesis of 4-[[(2,6-dichlorophenyl)carbonyl]amino]-N-[[1-((4-methylsulfonyl) butyl)cyclopentyl]carbonyl]-L-phenylalanine alcohol.

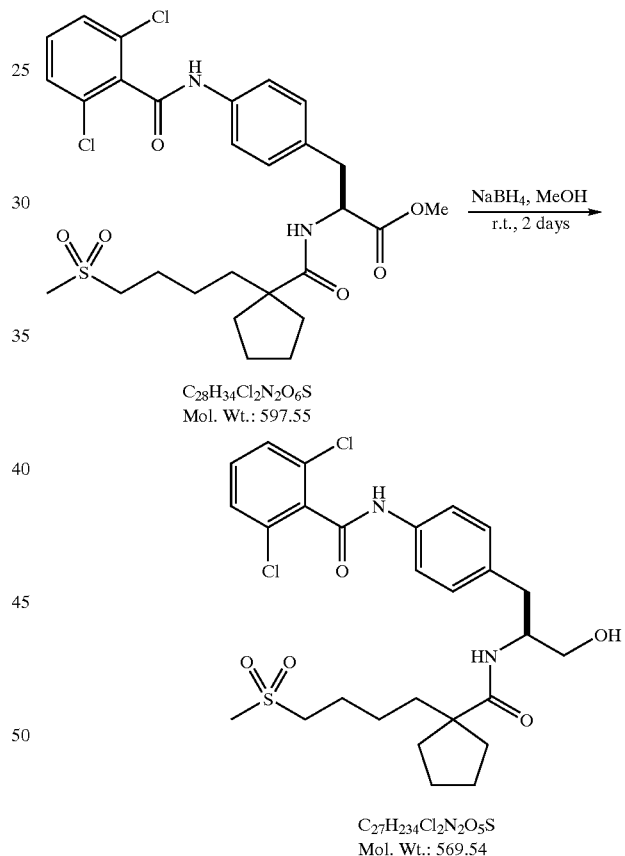

$C_{28}H_{34}Cl_2N_2O_6S$
Mol. Wt.: 597.55

$C_{27}H_{234}Cl_2N_2O_5S$
Mol. Wt.: 569.54

To a suspension of 4-[[(2,6-dichlorophenyl)carbonyl]amino]- N-[[1-((4-methylsulfonyl)butyl) cyclopentyl] carbonyl]-L-phenylalanine methyl ester (3.34 mmol, 2.0 g) in methanol (40 mL) was added excess sodium borohydride (10 mmol, 378 mg) in four portions during a period of 6 h at 30–35° C. The clear solution was stirred for 15 h at room temperature at which time TLC analysis of the mixture indicated the presence of starting material. Then, some more sodium borohydride (16.9 mmol, 640 mg) was added in four portions during a period of 6 h and the solution was stirred for another 3 days. The excess hydride was destroyed by a slow addition of water (10 mL). The methanol was removed under vacuum and the resulting solid was dissolved in a mixture of water (30 mL), saturated ammonium chloride (80 mL), ethyl acetate (100 mL) and tetrahydrofuran (50 mL) at hot condition. The two layers were separated and the aqueous layer was extracted with ethyl acetate (50 mL) and tetrahydrofuran (50 mL). The combined extracts were washed with brine solution (100 mL) and dried over anhydrous magnesium sulfate. After filtration of the drying agent, the filtrate was concentrated under vacuum and crude residue was purified by a silica gel column chromatography eluting with ethyl acetate to afford 0.89 g (47%) of 4-[[(2,6-dichlorophenyl)carbonyl]amino]-N-[[1-((4-methylsulfonyl)butyl)cyclopentyl] carbonyl]-L-phenylalanine alcohol as an amorphous white solid. HR MS: Obs.mass, 569.1645. Calcd. mass, 569.1643 (M+H).

Example 3.

Using the general procedure described in example 1, the following can be prepared:

4-[[(2-methyl-5-nitrophenyl)carbonyl]amino]-N-[[1-((4-methylsulfonyl)butyl)cyclopentyl]carbonyl]-L-phenylalanine alcohol 4-[[(2,6-dimethylphenyl)carbonyl]amino]-N-[[1-((4-methylsulfonyl)butyl)cyclopentyl]carbonyl]-L-phenylalanine alcohol 4-[[(2-trifluoromethylphenyl)carbonyl]amino]-N-[[1-((4-methylsulfonyl)butyl)cyclopentyl]carbonyl]-L-phenylalanine alcohol 4-[[(2-methyl-5-nitrophenyl)carbonyl]amino]-N-[[1 -((4-methylthio)butyl)cyclopentyl]carbonyl]-L-phenylalanine alcohol 4-[[(2,6-dichlorophenyl)carbonyl]amino]-N-[[1-((3-methylsulfonyl)propyl)cyclopentyl]carbonyl]-L-phenylalanine alcohol 4-[[(2,6-dichlorophenyl)carbonyl]amino]-N-[[1 -(2-methoxyethyl)cyclopentyl]carbonyl]-L-phenylalanine alcohol 4-[[(2,6-dichlorophenyl)carbonyl]amino]-N-[(2-methyl-6-ethylphenyl)carbonyl]-L-phenylalanine alcohol 4-[[(2,6-dichlorophenyl)carbonyl]amino]-N-[(2-trifluoromethylphenyl)carbonyl]-L-phenylalanine alcohol 4-[[(2,6-dimethylphenyl)carbonyl]amino]-N-[(2-bromophenyl)carbonyl]-L-phenylalanine alcohol 4-[[(2,6-dimethylphenyl)carbonyl]amino]-N-[(2-bromophenyl)carbonyl]-L-phenylalanine alcohol Alternate names for some of the above compounds are 4-[[(2-methyl-5-nitrophenyl)carbonyl]amino]-N-[[1-[4-(methylsulfonyl)butyl] cyclopentyl]carbonyl]-L-phenylalanine alcohol.

4-[[(2,6-dimethylphenyl)carbonyl]amino]-N-[[1-[4-(methylsulfonyl)butyl]cyclopentyl] carbonyl]-L-phenylalanine alcohol.

4-[[(2-trifluoro-methylphenyl) carbonyl]amino]-N-[[1-[4-(methylsulfonyl)butyl] cyclopentyl]carbonyl]-L-phenylalanine alcohol 49. 4-[[(2-methyl-5-nitrophenyl)carbonyl]amino]-N-[[1-[4-(methylthio)butyl] cyclopentyl]carbonyl]-L-phenylalanine alcohol 4-[[(2,6-dichlorophenyl)carbonyl]amino]-N-[[1-[3-(methylsulfonyl)propyl] cyclopentyl]carbonyl]-L-phenylalanine alcohol.

4-[[(2,6-dichlorophenyl) carbonyl]amino]-N-[[1 -(2-methoxyethyl)cyclopentyl]carbonyl]-L-phenylalanine alcohol 4-[[(2,6-dichlorophenyl)carbonyl]amino]-N-[[1-[4-[methylsulfonyl)butyl]cyclopentyl]-L-phenylalanine alcohol.

Example 4.

Acute airway inflammation in the atopic primate.

Airway inflammation in the monkey was determined using a modification of the protocol described by Turner et al. (Turner et al., 1994). Adult male cynomolgus monkeys (*Macaca fascicularis,* Hazelton Labs, Denver, Pa.) weighing between 3.6–5.8 kg were used in these studies. All animals exhibited positive skin and airway responses to Ascaris suum antigen and had at least a 3-fold increase in the sensitivity to methacholine (MCh) when subjected to an aerosol of ascaris extract.

On the day of each experiment the animals were anesthetized with ketamine hydrochloride, 12 mg/kg, and xylazine, 0.5 mg/kg, intubated with a cuffed endotracheal tube (3 mm, Mallinckrodt Medical, St. Louis, Mo.), then seated in an upright position in a specially designed Plexiglass chair (Plas-Labs, Lansing, Mich.). The endotracheal tube was connected to a heated Fleisch pneumotachograph. Airflow was measured via a Validyn differential pressure transducer (DP 45–24) that was attached to the pneumotachograph. Transpulmonary pressure was measured via a second Validyne transducer (DP 45–24) connected between a sidearm of the tracheal cannula and a 18-gauge intrapleural needle inserted in the intercostal space located below the left nipple. Recordings of pressure and flow and the calculation of $R_L$ were made using the Modular Instruments data acquisition system as described above. Baseline $R_L$ was measured for all animals on the day of each experiment and had an average value of about 0.04 cmH$_2$0/ml/sec.

Protocol

Airway inflammation was induced by exposing the animal to an aerosol of A. Suum extract for 60 sec. The aerosol was delivered via a nebulizer (De Vilbiss Model 5000, Healt Care Inc., Somerset, Pa.) that was attached to the endotracheal tube. The concentration of extract was predetermined for each animal (500 to 50,000 PNU) and caused at least a doubling in the airway resistance. At 24 hour after the antigen challenge, the animals were anesthetized as described previously and placed on a stainless steel table. Airway inflammation was assessed by inserting a pediatric bronchoscope into the airway lumen down to about the 4 or 5th generation bronchi and gently lavaging with 3 ×2 ml aliquots of sterile Hanks Balanced Salt Solution. The recovered lavage fluid then was analyzed for the total cell and differential cell counts using standard hematological techniques.

Drug Treatment

The animals received drug or a vehicle, p.o., administered 2 hours prior to antigen challenge. The compound of example 1 caused a significant decrease in the number and percent of inflammatory cells present in the lavage fluid relative to vehicle treated control animals.

What is claimed is:

1. A compound of the formula:

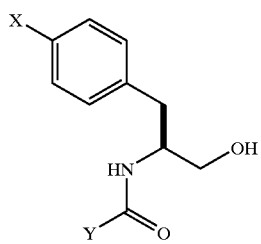

wherein:

X is

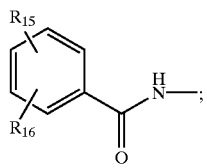

$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aroyl, aryl, aryloxy;

$R_{16}$ is hydrogen, halogen, nitro, cyano, lower alkyl, OH, perfluorolower alkyl, or lower alkylthio; Y is a phenyl moiety of the formula:

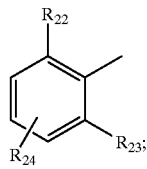

$R_{22}$ and $R_{23}$ are independently hydrogen, lower alkyl, lower alkoxy, lower cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen;

$R_{24}$ is hydrogen, lower alkyl, lower alkoxy, aryl, nitro, cyano, lower alkyl sulfonyl, or halogen.

2. A compound of claim 1 wherein $R_{15}$ is lower alkyl, nitro, halogen, perfluoromethyl, or cyano and $R_{16}$ is independently hydrogen, lower alkyl, nitro, halogen, perfluoromethyl, or cyano.

3. A compound of claim 2 wherein $R_{15}$ and $R_{16}$ are independently chloro or fluoro.

4. A compound of claim 2 wherein X is selected from the group of

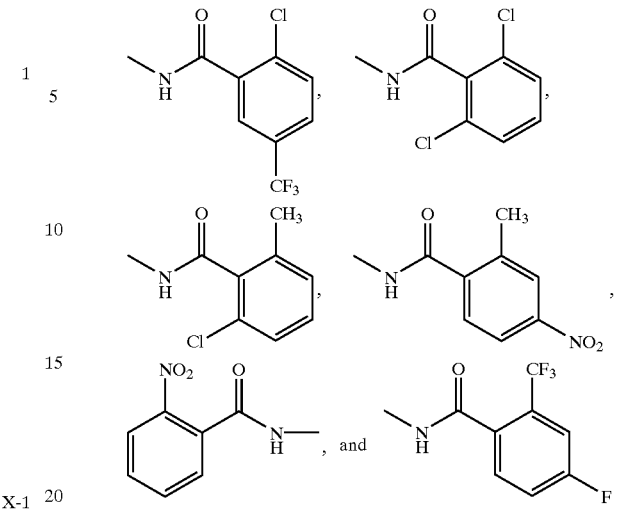

5. A compound of claim 1 wherein $R_{22}$ and $R_{23}$ are lower alkyl, trifluoromethyl, or halogen and $R_{24}$ is hydrogen, lower alkyl, lower alkoxy, or halogen.

6. A compound of claim 5 wherein Y-1 is selected from the group of

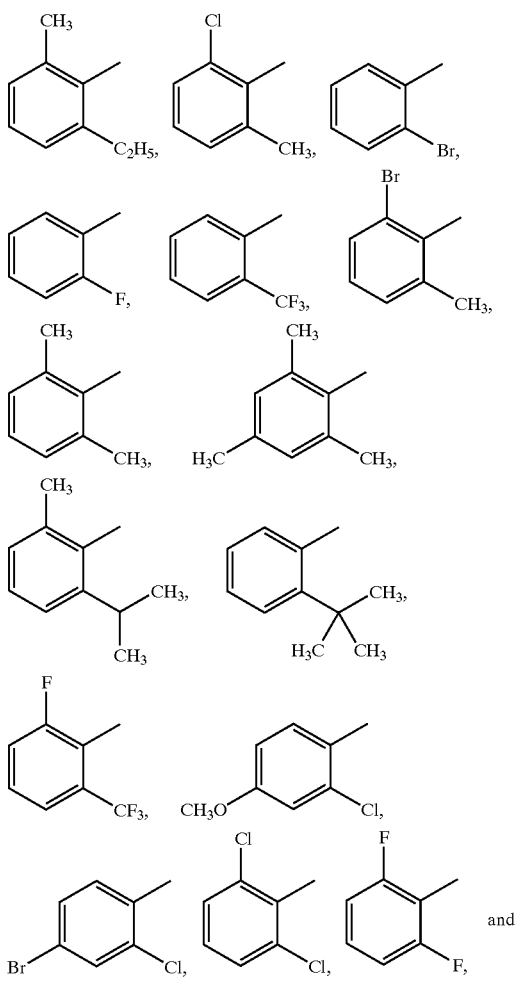

-continued

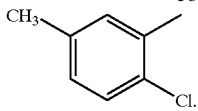

7. A compound of claim 1 where X is

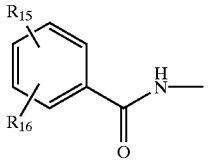

$R_{16}$ hydrogen is lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl, and Y is a group of the formula Y-1

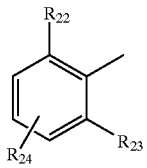

where $R_{22}$ is hydrogen, halogen, trifluoroalkyl, or lower alkyl and $R_{23}$ is halogen, trifluoroalkyl, or lower alkyl, and $R_{24}$ is hydrogen.

8. A compound of claim 7 wherein X is a group of the formula X-1

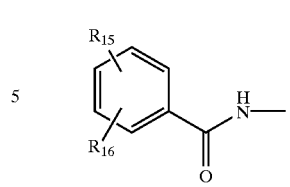

$R_{16}$ is hydrogen, lower alkyl, nitro, cyano, halogen, lower alkylthio, perfluoroloweralkyl and $R_{15}$ is lower alkyl, nitro, cyano, halogen, lower alkylsulfonyl, perfluoroloweralkyl; and Y is

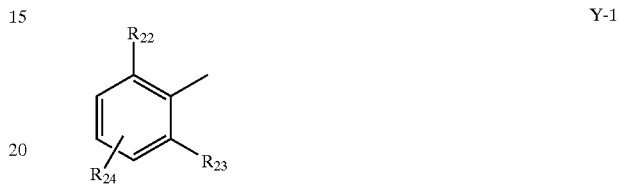

where $R_{22}$ is hydrogen, halogen, or lower alkyl and $R_{23}$ is halogen or lower alkyl, and $R_{24}$ is hydrogen.

9. A compound of claim 8 wherein $R_{16}$ is hydrogen or halogen and $R_{15}$ is halogen; $R_{22}$ is hydrogen, halogen, ethyl, or methyl and $R_{23}$ is halogen, ethyl, or methyl.

10. A compound of claim 8 wherein $R_{15}$ is lower alkyl or halogen and $R_{16}$ is hydrogen, lower alkyl, halogen and $R_{22}$ and $R_{23}$ is ethyl or lower alkyl or halogen.

11. The compound of claim 10 wherein said compound is 4-[[(2,6-dichloro-phenyl)carbonyl]amino]-N-[(2-chloro-6-methylphenyl)carbonyl]-L-phenylalaninol.

12. The comound of claim 10 wherein said compound is 4-[[(2,6-dichloro-phenyl)carbonyl]amino]-N-[(2-bromophenyl)carbonyl]-L-phenylalanine alcohol.

13. The compound of claim 8 wherein $R_{15}$ and $R_{16}$ are hydrogen, lower alkyl or halogen.

14. The compound of claim 13 wherein said compound is 4-[[(2,6-dichloro-phenyl)carbonyl]amino]-N-[(2-bromophenyl)carbonyl]-L-phenylalanine alcohol.

15. The compound of claim 13 wherein said compound is 4-[[(2,6-dimethylphenyl)carbonyl]amino]-N-[(2-bromophenyl)carbonyl]-L-phenylalanine alcohol.

* * * * *